US006962785B2

(12) United States Patent
Agris et al.

(10) Patent No.: US 6,962,785 B2
(45) Date of Patent: Nov. 8, 2005

(54) ANTIBACTERIAL AND ANTIVIRAL AGENTS AND METHODS OF SCREENING FOR THE SAME

(75) Inventors: Paul F. Agris, Raleigh, NC (US); Salman Ashraf, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 132 days.

(21) Appl. No.: 10/212,905

(22) Filed: Aug. 6, 2002

(65) Prior Publication Data

US 2003/0008808 A1 Jan. 9, 2003

Related U.S. Application Data

(63) Continuation of application No. 09/315,674, filed on May 20, 1999, now Pat. No. 6,461,815.
(60) Provisional application No. 60/086,380, filed on May 22, 1998.

(51) Int. Cl.[7] .......................... C12Q 1/68; C07H 21/02; C07H 21/04
(52) U.S. Cl. .......................... 435/6; 536/23.1; 536/24.1
(58) Field of Search ........................ 435/236, 4; 436/6; 536/23.1, 24.1

(56) References Cited

U.S. PATENT DOCUMENTS

| 5,358,862 A | 10/1994 | Hardesty et al. |
| 5,556,840 A | 9/1996 | Suhadolnik et al. ........... 514/44 |
| 5,629,188 A | 5/1997 | Shiba et al. |
| 5,674,729 A | 10/1997 | Wimmer et al. ......... 435/235.1 |
| 5,712,096 A | 1/1998 | Stern et al. |
| 5,821,052 A | 10/1998 | Chen et al. |

FOREIGN PATENT DOCUMENTS

| ES | 2040615 | 5/1991 | ............ C12N/7/02 |
| JP | 60-196197 | 10/1985 | ............ C12P/21/02 |

OTHER PUBLICATIONS

Crooke, S.T., Antisense Research and Application, Chapter 1, Springer–verlag, (New York. 1998).*
Branch A.D . . . TIBS. vol. 23. p. 45–50 (Feb. 1998).*
Stein. C.A . . . Nature Biotechnology vol. 17. pp. 751–752 (Aug. 1999).*
Flanagan. W.M.S et al . . . Nature Biotechnology. vol. 17 p. 48–52 (Jan. 1999).*
Lloyd. A.W. DDT, vol. 2. No. 10 (Oct. 1997).*
Goodman. M . . . DDT, vol. 2. No. 9. (Sep. 1997).*
Wess, G., DDT vol. 1. No. 12 (Dec. 1996).*
Dirani–Diab et al., Antimicrobial Agents and Chemotherapy, 1997, vol. 41, p 2141–2148.*
Sarih–Cotton et al., "Preferential interaction of HIV reverse transcriptase with two regions of primer tRNALys as evidenced by footprinting studies and inhibition with synthetic oligoribonucleotides", Journal of Molecular Biology, 1992, vol. 226, p. 1–6.*

Agris, et al., *Unique Structure Explains Human tRNA(Lys3) Selection by HIV Reverse Transcriptase*, Presented at the RNA Society 1996 Meeting (Feb. 15, 1996).
Agris, et al., *Unique Structure Explains Unusual Biochemical Properties of tRNA(Lys)SUU*, Presented at the ASBMB 1996 Meeting (Jan. 30, 1996).
Ashraf, S. Salman, et al., *Single atom modification (O–>S) of tRNA confers ribosome binding*, RNA, vol. 5, pp. 188–194 (1999).
Baldwin, John J., et al., *Recent Advances in the Generation of Small–Molecule Combinatorial Libraries: Encoded Split Synthesis and Solid–Phase Synthetic Methodology*, Medicinal Research Reviews, vol. 16, No. 5, pp. 391–405 (1996).
Brierley, Ian, et al., *Expression of a Coronavirus Ribosomal Frameshift Signal in Escherichia coli: Influence of tRNA Anticodon Modification on Frameshifting*, J. Mol Biol., vol. 270, pp. 360–373 (1997).
Guenther, et al., *Modified RNAs as potential drug targets*, Acta Biochimica Polonica, vol. 45, No. 1, pp. 13–18 (1998).
Heurgué–Hamard, Valérie, et al., *The growth defenct in Escherichia coli deficient in peptidyl–tRNA hydrolase is due to starvation for Lys–tRNA$^{Lys}$*, EMBO Journal, vol. 15, No. 11, pp. 2826–2833 (1996).
Kumar, Raju K., et al., *Synthesis and studies on the effect of 2–thiouridine and 4–thiouridine on sugar conformation and RNA duplex stability*, Nucleic Acids Research, vol. 25, No. 6, pp. 1272–1280 (1997).
McClain, William H., et al., *Nucleotides that determine Escherichia coli tRNA$^{Arg}$ and tRNA$^{Lys}$ acceptor identities revealed by analyses of mutant opal and amber suppressor tRNAs*, Proc. Natl. Acad. Sci. USA, vol. 87, pp. 9260–9264 (Dec. 1990).
Penner, Michael, et al., *Phase T4–coded Stp: Double–Edged Effector of Coupled DNA and tRNA–Restriction Systems*, J Mol. Biol., vol. 249, pp. 857–868 (1995).
Sprinzl, Mathias, et al., *Compilation of tRNA sequences and sequences of tRNA genes*, Nucleic Acids Research, vol. 26, No. 1, pp. 148–153 (1998).

(Continued)

*Primary Examiner*—Andrew Wang
*Assistant Examiner*—Tracy Vivlemore
(74) *Attorney, Agent, or Firm*—Myers Bigel Sibley & Sajovec, P.A.

(57) ABSTRACT

A method of screening for compounds useful for inhibiting retrovirus propagation in a host for the retrovirus, wherein the retrovirus primes reverse transcription in the host by binding of a specific host tRNA to retrovirus RNA at at least a pair of separate binding sites on the host tRNA, comprises contacting the specific host tRNA to the retrovirus RNA in the presence of the test compound, and then determining whether the compound inhibits the binding of the specific host tRNA to the retrovirus RNA in the presence of the test compound.

5 Claims, 6 Drawing Sheets

OTHER PUBLICATIONS

Stryer, *Biochemistry*, 3d Edition, W. H. Freeman and Co., New York, p. 759 (1988).

Tamura, Koji, et al., *In vitro study of E.coli tRNA$^{Arg}$ and tRNA$^{Lys}$ identity elements, Nucleic Acids Research*, vol. 20, No. 9, pp. 2335–2339 (1992).

Van Ahsen, J., et al., *Identification of 2'–hydroxyl Groups Required for Interaction of a rTNA Anticodon Stem–Loop Region with theRibosome, RNA*, vol. 3, pp. 49–56 (Jan. 1997).

Watanabe, Kimitsuna, et al., *Unusual anticodon loop structure found in E.coli lysine tRNA Nucleic Acids Research*, vol. 22, No. 1, pp. 79–87 (1994).

Branch, A.D., *TIBS*, vol. 23, pp. 45–50 (Feb. 1998).

Stein, C.A., *Nature Biotechnology*, vol. 17, pp. 751–752 (Aug. 1999).

Flanagan, W.M., et al., *Nature Biotechnology*, vol. 17, pp. 48–52 (Jan. 1999).

Crooke, S.T., *Antisense Research and Application (Ed. Stanley Crooke)*, Chapter 1, Springer–Verlag, (New York, 1998).

Goodman, M., *DTT*, vol. 2, No. 9, (Sep. 1997).

Lloyd, A.W., *DTT*, vol. 2, No. 10 (Oct. 1997).

Wess, G., *DTT*, vol. 1, No. 12 (Dec. 1996).

\* cited by examiner

N6-THREONYLCARBAMOYL-ADENOSINE, t6A-

ANTIBACTERIAL AND ANTIVIRAL AGENTS AND METHODS OF SCREENING FOR THE SAME

RELATED APPLICATIONS

This application is a continuation of U.S. patent application Ser. No. 09/315,674, filed May 20, 1999, now issued as U.S. Pat. No. 6,461,815, which in turn claims the benefit of U.S. provisional application Ser. No. 60/086,380, filed May 22, 1998, the disclosures of which are incorporated by reference herein in their entirety.

This invention was made with government support under grant number GM23037 from the National Institutes of Health and grant number MCB 9631103 from the National Science Foundation. The Government has certain rights to this invention.

FIELD OF THE INVENTION

The present invention concerns antibacterial and antiviral agents that are directed against tRNA targets, and methods of screening for antibacterial and antiviral agents directed against tRNA targets.

BACKGROUND OF THE INVENTION

Numerous common bacteria are capable of mutating to become resistant to antibiotic agents. Viruses such as HIV are also known to mutate rapidly and thereby avoid immune defense mechanisms. Accordingly, there is a continued need for new antimicrobial agents and antiviral agents.

J. Hill et al., PCT Application WO 9705132, describe compounds that inhibit isoleucyl-tRNA synthetases. The compounds are stated to be useful against a broad spectrum of bacteria, fungi and parasites.

SUMMARY OF THE INVENTION

A first aspect of the present invention is a method of inhibiting microbe propagation. The method comprises inhibiting ribosomal binding of a specific microbial tRNA such as $tRNA^{lys}_{SUU}$, $tRNA^{gln}_{SUG}$ or $tRNA^{glu}_{SUC}$ (for example, at position 27–43, most preferably position 34, thereof) in the microbe by an amount sufficient to inhibit microbe propagation. This is achieved by a drug or compound binding to positions 27–43 (one or more positions simultaneously), most preferably position 34 or 37 of the tRNA. Additionally, the compound or drug can inactive (in the microbe) one or more enzymes that are responsible for producing the modification in the specific microbial tRNA that is responsible for the specific binding properties thereof (at positions 27 to 43, preferably positions 34 or 43).

A second aspect of the present invention is a method of inhibiting retrovirus propagation in a host for that retrovirus, wherein that retrovirus primes reverse transcription by binding of a specific host tRNA to retrovirus RNA at at least a pair of separate binding sites. The method comprises inhibiting the binding of the specific host tRNA to the retrovirus RNA at one of the binding sites by an amount sufficient to inhibit propagation of the retrovirus in the host. Advantageously, mutation of the retrovirus RNA to bind an alternate host tRNA for priming of reverse transcription requires a pair of mutations in at least the pair of separate tRNA binding sites in the retrovirus RNA: a low probability event.

A third aspect of the present invention is a method of screening for compounds useful for inhibiting microbial propagation. The method comprises contacting a specific microbial tRNA (for example, $tRNA^{lys}_{SUU}$) to a ribosome that binds that tRNA in the presence of the test compound, and then determining whether the compound inhibits the binding of that tRNA (e.g., binding of $tRNA^{lys}_{SUU}$, $tRNA^{gln}_{SUG}$ or $tRNA^{glu}_{SUC}$ at position 27–43, most preferably position 34, thereof) to the ribosome. The inhibition of binding indicates that the test compound is useful for inhibiting microbial propagation. The test compound will generally be binding to position 27–43, individually or in combination, most preferably positions 34 and or 37 of the stated tRNAs. The screening step may be carried out in a host cell, wherein the corresponding host cell tRNA (i.e., the tRNA that binds to the same amino acid) is modified differently as compared to said microbial tRNA at position 27 through 43 thereof (i.e., has a different modification, is not modified where the microbial tRNA is modified, or has the same modification but in a structure not recognized or specifically bound by the test compound).

A fourth aspect of the invention is a method of screening for compounds useful for inhibiting retrovirus propagation in a host for the retrovirus, wherein the retrovirus primes reverse transcription in the host by binding of a specific host tRNA to retrovirus RNA at at least a pair of separate binding sites on the host tRNA. The method comprises contacting the specific host tRNA to the retrovirus RNA in the presence of the test compound, and then determining whether the compound inhibits the binding of the specific host tRNA to the retrovirus RNA in the presence of the test compound. The inhibition of binding indicates that the test compound is useful for inhibiting propagation of the virus in the host. Again, note that mutation of the retrovirus RNA to bind an alternate host tRNA for priming of reverse transcription requires at least a pair of separate mutations at different tRNA binding sites in the retrovirus RNA.

The foregoing and other objects and aspects of the present invention are explained in detail in the drawings herein and the specification set forth below.

DETAILED DESCRIPTION OF THE INVENTION

Figure 1A:
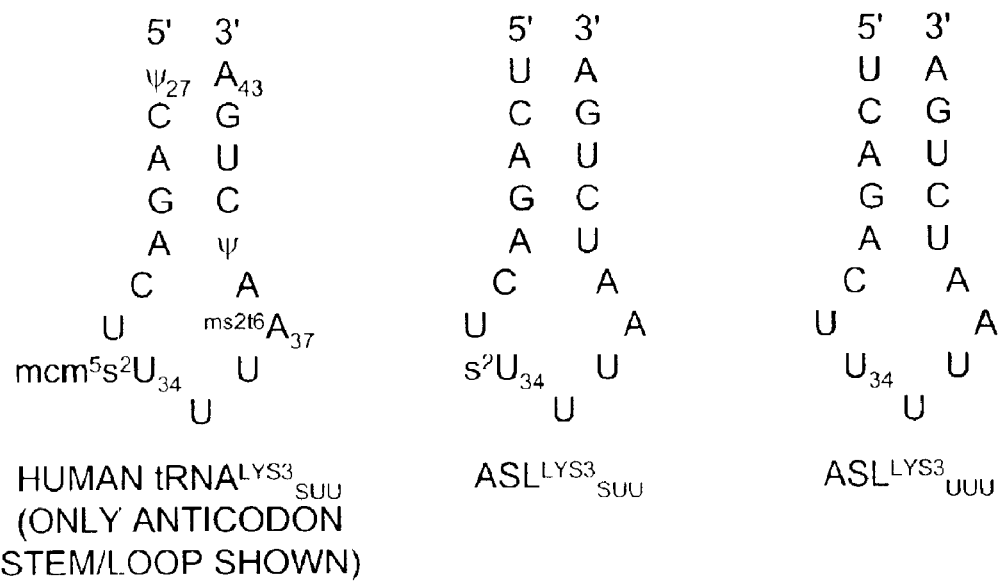
FIG. 1. Nucleotide sequences of human $tRNA^{Lys3}$ anticodon stem/loops and structures of modified uridines. A: Nucleotide sequences of the anticodon stem/loops (ASLs) of native human $tRNA^{Lys3}_{SUU}$ and that of the chemically synthesized $tRNA^{Lys}$ ASLs used in the experiments: $ASL^{Lys3}_{SUU}$ and $ASL^{Lys3}_{SUU}$. B: Chemical structures of $mcm^5s^2U$ (modified $U_{34}$ in human $tRNA^{Lys3}_{SUU}$), $mnm^5s^2U$ (modified $U_{34}$ in E. coli $tRNA^{Lys}_{SUU}$), and $s^2U$ in $ASL^{Lys3}_{SUU}$. Modified nucleosides: $\psi$=pseudouridine; $mcm^5s^2U$=5-methoxycarbonylmethyl-2-thiouridine; $mnm^5s^2U$=5-methylaminomethyl-2-thiouridine; $ms^2t^6A$=2-methylthio-$N^6$-threonylcarbamoyl-adenosine; $s^2U$=2-thiouridine. Human and E. coli $tRNA^{Lys}_{SUU}$ anticodon stem-loop domains have identical sequences except for the three base pairs at the top of the stem (P. Agris et al., *RNA* 3: 420–428 (1997).
Figure 1B:
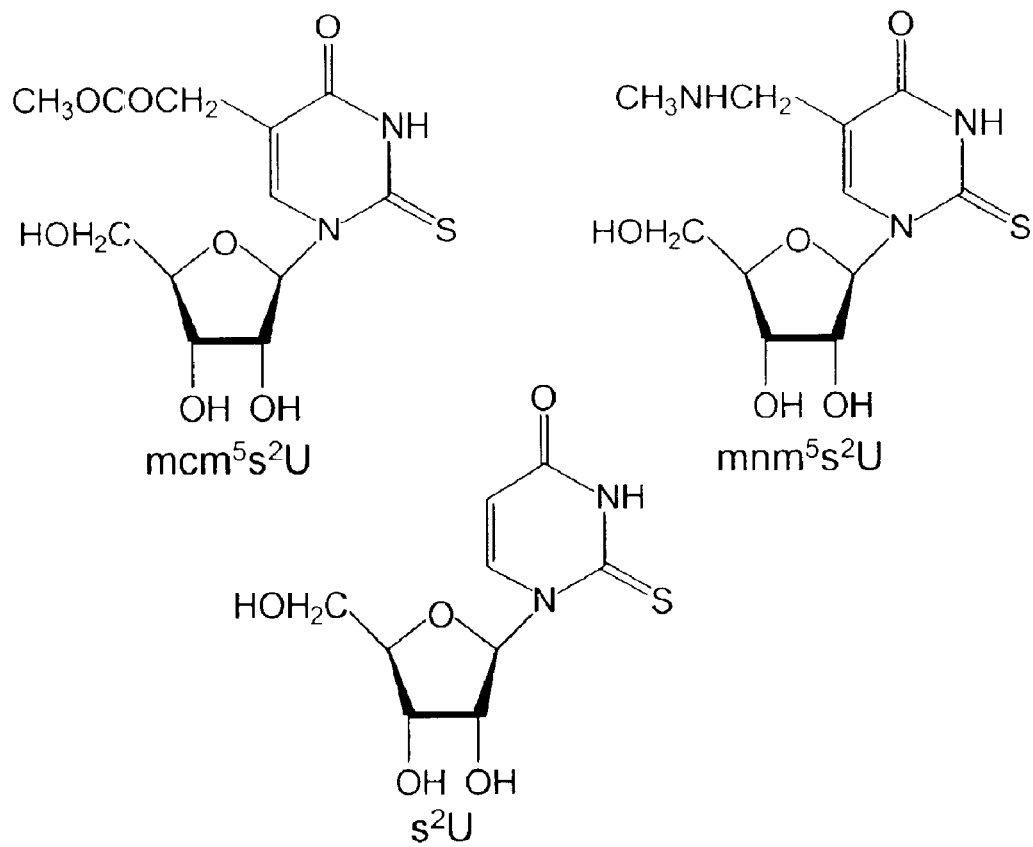

The term "microbe" as used herein includes bacteria, yeast, fungi and protozoans. Bacteria, including both gram positive and gram negative bacteria, are preferred. Examples of suitable bacteria include, but are not limited to, *Escherichia coli, Staphylococcus aureus*, and *Helicobacter pylon*.

The term "host" as used herein refers to human or animal cells or tissues in vitro and human or animal subjects (e.g., avian or mammalian cells, tissues and subjects such as chickens, turkeys, mouse, rat, cats, dogs, cows, pigs, horses, etc.).

The term "ribosome" as used herein refers to both intact active ribosomes and ribosome subunits that retain tRNA binding, such as 30S subunits.

The specific tRNA referred to herein with respect to microbe tRNA is preferably a unique or unusual tRNA: that is, one that contains one or more modified bases other than adenine, guanine, cytosine, or uracil in the anticodon binding region (including both the stem and loop thereof), and/or preferably one that is the only tRNA available in that microbe for binding to a corresponding amino acid (e.g., lysine) during protein translation in the corresponding microbe. Preferably the modified base or bases is/are a nucleotide(s) that is/are at a binding site as described below (e.g., nucleotides 27 through 43) and participates in the binding event. Where carried out in vivo, the tRNA for the corresponding amino acid bound by the microbe tRNA preferably does not have the same modified base at the binding site or corresponding nucleotide in the host organism (i.e., pathogen specific modification). Many of these exist in the human host and in agronomically important animal hosts as set forth above). Examples of modified bases are set forth in Table 1 below.

TABLE 1

Standard and modified nucleosides in tRNA and their standard abbreviations.

| | |
|---|---|
| U | uridine |
| C | cytidine |
| A | adensoine |
| G | guanosine |
| T | thymidine |
| ?A | unknown modified adenosine |
| m1A | 1-methyladenosine |
| m2A | 2-methyladenosine |
| i6A | N$^6$-isopentenyladenosine |
| ms2i6A | 2-methylthio-N$^6$-isopentenyladenosine |
| m6A | N$^6$-methyladenosine |
| t6A | N$^6$-threonylcarbamoyladenosine |
| m6t6A | N$^6$-methyl-N$^6$-threonylcarbomoyladenosine |
| ms2t6A | 2-methylthio-N$^6$-threonylcarbamoyladenosine |
| Am | 2'-O-methyladenosine |
| I | Inosine |
| m1I | 1-methylinosine |
| Ar(p) | 2'-O-(5-phospho)ribosyladenosine |
| io6A | N$^6$-(cis-hydroxyisopentenyl)adenosine |
| ?C | Unknown modified cytidine |
| s2C | 2-thiocytidine |
| Cm | 2'-O-methylcytidine |
| ac4C | N$^4$-acetylcytidine |
| m5C | 5-methylcytidine |
| m3C | 3-methylcytidine |
| k2C | lysidine |
| f5C | 5-formylcytidin |
| f5Cm | 2'-O-methyl-5-formylcytidin |
| ?G | unknown modified guanosine |
| Gr(p) | 2'-O-(5-phospho)ribosylguanosine |
| m1G | 1-methylguanosine |
| m2G | N$^2$-methylguanosine |
| Gm | 2'-O-methylguanosine |
| m22G | N$^2$N$^2$-dimethylguanosine |
| m22Gm | N$^2$,N$^2$,2'-O-trimethylguanosine |
| m7G | 7-methylguanosine |
| fa7d7G | archaeosine |
| Q | queuosine |
| manQ | mannosyl-queuosine |
| galQ | galactosyl-queuosine |
| yW | wybutosine |
| o2yW | peroxywybutosine |
| ?U | unknown modified uridine |
| mnm5U | 5-methylaminomethyluridine |
| s2U | 2-thiouridine |
| Um | 2'-O-methyluridine |
| s4U | 4-thiouridine |
| ncm5U | 5-carbamoylmethyluridine |
| mcm5U | 5-methoxycarbonylmethyluridine |
| mnm5s2U | 5-methylaminomethyl-2-thiouridine |
| mcm5s2U | 5-methoxycarbonylmethyl-2-thiouridine |
| cmo5U | uridine 5-oxyacetic acid |
| mo5U | 5-methoxyuridine |
| cmnm5U | 5-carboxymethylaminomethyluridine |
| cmnm5s2U | 5-carboxymethylaminomethyl-2-thiouridine |
| acp3U | 3-(3-amino-3-carboxypropyl)uridine |
| mchm5U | 5-(carboxyhydroxymethyl)uridinemethyl ester |
| cmnm5Um | 5-carboxymethylaminomethyl-2'-O-methyluridine |
| ncm5Um | 5-carbamoylmethyl-2'-O-methyluridine |

TABLE 1-continued

Standard and modified nucleosides in tRNA and their standard abbreviations.

| | |
|---|---|
| D | Dihydrouridine |
| Ψ | pseudouridine |
| m1Ψ | 1-methylpseudouridine |
| Ψm | 2'-O-methylpseudouridine |
| m5U | ribosylthymine |
| m5s2U | 5-methyl-2-thiouridine |
| m5Um | 5,2'-O-dimethyluridine |

See Sprinzl et al., Nucleic Acids Res. 26, 148 (1998).

The specific tRNA referred to herein with respect to host tRNA is also preferably a unique or unusual tRNA: that is, one that contains one or more modified bases other than adenine, guanine, cytosine, or uracil in the anticodon binding region (including both the stem and loop thereof), as set forth above, and/or preferably one that is the only tRNA available in that host for binding to retroviral RNA for priming of reverse transcription of that retroviral RNA in the host.

The region of the tRNA to which binding occurs as described herein is, in general, the tRNA anticodon stem-loop structure, and most preferably the loop structure itself. Following conventional tRNA nucleotide numbering (see, e.g., M. Sprinzl et al., Compilation of tRNA sequences and sequences of tRNA genes, Nucleic Acids Res. 26, 148–153 (1998)), the site to which binding occurs is from nucleotide 27 or 32 to nucleotide 39, 41 or 43. Nucleotides 32, 34, 35, 37 and 39 are preferred binding sites, and nucleotides 34 and 37 are particularly preferred binding sites. Binding may be to a single site or combination of sites comprising nucleotides within this range.

As noted above, a method of screening for compounds useful for inhibiting microbial propagation is disclosed herein. The method involves contacting a specific microbial tRNA such as $tRNA^{lys}_{SUU}$, $tRNA^{gln}_{SUG}$, or $tRNA^{glu}_{SUC}$ to a ribosome that binds that tRNA in the presence of the test compound. The contacting step is typically carried out in vitro in an aqueous solution, with the tRNA, the ribosome, an appropriate messenger RNA, and the test compound in the aqueous solution. The contacting step may be carried out with a single test compound or with a library of probes or test compounds in any of a variety of combinatorial chemistry systems, as discussed in greater detail below.

After the contacting step, the next step involves determining whether the compound inhibits the binding of the specific tRNA to the ribosome (e.g., the binding of $tRNA^{lys}_{SUU}$ at position 34 thereof to the ribosome).

The determining step can be carried out by any suitable means, such as the filter binding assays disclosed below, or in any of the binding detection mechanisms commonly employed with combinatorial libraries of probes or test compounds as discussed below. Inhibition of ribosomal binding by the test compound indicates that the test compound is useful for inhibiting microbial (e.g., bacterial, protozoal, fungal) propagation. Compounds identified by this technique are sometimes referred to as "active compounds" herein. The method is particularly useful for identifying compounds that inhibit bacterial growth, preferably bacteria that contain a single tRNA for a particular amino acid, such as a single lysine tRNA, particularly where the lysine tRNA contains a 2-thiouridine at position 34. Examples of such bacteria include, but are not limited to, Helicobacter pylori, Escherichia coli and Staphylococcus aureus. Examples of such 2-thiouridine bases include, but are not limited to:

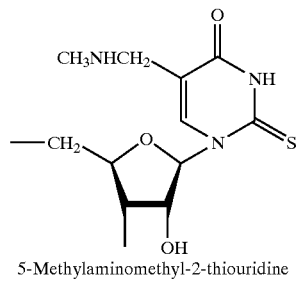

5-Methylaminomethyl-2-thiouridine

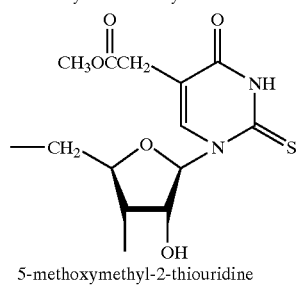

5-methoxymethyl-2-thiouridine

A method of screening for compounds useful for inhibiting retrovirus propagation in a host for the retrovirus, particularly where the retrovirus primes reverse transcription in the host by binding of a specific host tRNA to retrovirus RNA at a pair of separate binding sites on the host tRNA, is also disclosed herein. The method comprises contacting the specific host tRNA to the retrovirus RNA in the presence of the test compound. The contacting step is typically carried out in vitro in an aqueous solution, with the tRNA, the retroviral RNA, and the test compound in the aqueous solution. The term "retroviral RNA" is intended to encompass both a complete retroviral genome and fragments thereof that contain the tRNA binding portions (such fragments will typically be at least 10 or 12 to 50 or more nucleotides in length). The contacting step may again be carried out with a single test compound or with a library of probes or test compounds in any of a variety of combinatorial chemistry systems, as discussed in greater detail below.

After the contacting step, the next step involves determining whether the compound inhibits the binding of the specific host tRNA to the retrovirus RNA in the presence of the test compound. The determining step can be carried out by any suitable means, such as gel shift assays, chemical and enzymatic footprinting, circular dichroism and NMR spectroscopy, equilibrium dialysis, or in any of the binding detection mechanisms commonly employed with combinatorial libraries of probes or test compounds as discussed below. The inhibition of binding indicates that the test compound is useful for inhibiting propagation of the virus in the host. Such compounds are also sometimes referred to as "active compounds" herein. The method may be carried out with retroviruses in general, particularly lentiviruses such as HIV-1. In one embodiment the specific host tRNA is mammalian, preferably primate or specifically human, such as $tRNA^{lys}_{SUU}$, and the determining step comprises determining whether the compound inhibits the binding of $tRNA^{lys}_{SUU}$ (for example at position 34 thereof) to the retrovirus RNA.

As noted above, the present invention can be used with test compounds (or "probe molecules"), or libraries (where groups of different probe molecules are employed), of any type. In general, such probe molecules (including those that are active compounds herein) are organic compounds, including oligomers such as antisense oligonucleotides, non-oligomers, organo-metallic compounds, and combinations thereof, as well as bio-inorganic compounds. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, and combinations thereof. Oligomers include peptides (that is, oligopeptides) and proteins, oligonucleotides such as DNA, RNA and their derivatives such as peptide nucleic acid (PNA), oligosaccharides, polylipids, polyester, polyamides, polyurethans, polyureas, polyethers, poly(phosphorus derivatives) such ass phosphates, phosphonates, phosphoramides, phosphonamides, phosphites, phosphinamides, etc., poly(sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecules may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety); J. Baldwin and I. Henderson, *Recent Advances in the Generation of Small-Molecule Combinatorial Libraries: Encoded Split Synthesis and Solid-Phase Synthetic Methodology*, Med. Res. Reviews 16, 391–405 (1996).

Such probe molecules or active compounds could be used as inhibitors by contacting the tRNA, the RNA to which the tRNA binds (mRNA, viral RNA) or the modification enzyme responsible for the unique or unsual chemistry or structure of the tRNA (i.e., the modified base).

A method of inhibiting microbe propagation comprises inhibiting ribosomal binding of a specific microbial tRNA (e.g., $tRNA^{lys}_{SUU}$, for example at position 34 thereof) in the microbe by an amount sufficient to inhibit microbe propagation. Inhibition of ribosomal binding may be carried out by contacting an active compound to the ribosome in an amount effective to inhibit binding suffuciently to inhibit microbe propagation. The microbe is preferably a bacteria, and most preferably a bacteria that contains a single lysine tRNA, and wherein the lysine tRNA contains a 2-thiouridine (this term including derivatives thereof) at position 34 thereof. Examples include but are not limited to *Escherichia coli* and *Staphylococcus aureus*. The microbe may be in vitro, in a culture media, or on a surface to be disinfected, or may be in vivo in a host (e.g., a human or animal host in need of an antimicrobial treatment). Formulations of active compounds can be prepared and administered in accordance with known techniques, as discussed below.

A method of inhibiting retrovirus propagation in a host for that retrovirus, wherein the retrovirus primes reverse transcription by binding of a specific host tRNA to retrovirus RNA at a pair of separate binding sites on the host tRNA, comprises inhibiting the binding of the specific host tRNA to the retrovirus RNA at one of the binding sites by an amount sufficient to inhibit propagation of the retrovirus in the host. Note that mutation of the retrovirus RNA to bind an alternate host tRNA for priming of reverse transcription requires a pair of mutations at separate tRNA binding sites in the retrovirus RNA. Formulations of active compounds can be prepared and administered in accordance with known techniques, as discussed below. In a preferred embodiment, the specific host tRNA is $tRNA^{lys}_{SUU}$, where binding may for example be inhibited at position 34 thereof. Preferably the retrovirus primes reverse transcription in the host specifically with the specific host tRNA, such as $tRNA^{lys}_{SUU}$. The method may be carried out with retroviruses in general, particularly lentiviruses such as HIV-1. The host may be a cell in vitro, or a human or animal subject in need of such treatment.

Subjects to be treated by the methods of the present invention are typically human subjects although the methods may be carried out with animal subjects (dogs, cats, horses, cattle, etc.) for veterinary purposes. The present invention provides pharmaceutical formulations comprising the active compounds, including pharmaceutically acceptable salts thereof, in pharmaceutically acceptable carriers for aerosol, oral, and parenteral administration as discussed in greater detail below. The therapeutically effective dosage of any specific compound, the use of which is in the scope of present invention, will vary somewhat from compound to compound, patient to patient, and will depend upon the condition of the patient and the route of delivery.

In accordance with the present method, an active compound or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the active compound or salt should be in the form of a plurality of solid particles or droplets having a particle size from about 0.5 to about 5 microns, preferably from about 1 to about 2 microns.

The present invention also provides new pharmaceutical compositions suitable for intravenous or intramuscular injection. The pharmaceutical compositions comprise an active compound or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain antimicrobial agents. Useful antimicrobial agents include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising an active compound or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the active compounds, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds or salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the compound, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble active compound or a salt thereof, in a carrier which comprises water. A surfactant may be present which lowers the surface tension of the formulation sufficiently to result in the formation of droplets within the desired size range when subjected to nebulization.

The present invention is explained in greater detail in the following non-limiting Examples.

EXAMPLES

1. Materials and Methods

Native tRNAs, transcripts, ASLs and 30S ribosomal subunits. Native yeast tRNA$^{Phe}_{GmAA}$, E. coli tRNA$^{Lys}_{SUU}$, and E. coli tRNA$^{Glu}_{SUC}$ were purchased from Sigma Chemical Company. In vitro transcripts of human tRNA$^{Lys3}_{UUU}$, E. coli tRNA$^{Glu}_{UUC}$ and E. coli tRNA$^{Gln}_{UUC}$ were gifts from Drs. Musier-Forsyth and Rodgers and Söll, respectively. ASLs, with and without s$^2$U, were synthesized using an adaptation of standard solid phase chemistry for RNA synthesis and purified by HPLC (Agris et al., *Biochimie* 77: 125–134 (1995); Kumar and Davis, *Nucleic Acids Res.* 25: 1272–1280(1997)). Sequence and modification of the ASLs were confirmed by MALDI mass spectroscopy (Faulstich et al., *Anal. Chem.* 69: 4349–4353 (1997)), nucleoside composition analysis (Gehrke and Kuo, *Chromatography and modification of nucleoside* Vol. 45A, ppA3-A71 (Amsterdam: Elsevier 1990) and organomercurial-gel electrophoresis (Igloi, *Biochemistry* 27: 3842–3849 (1998)). Both mass spectroscopy and HPLC analyses confirmed the purity of ASL$^{Lys3}_{SUU}$ to be greater than 90%. Thermal denaturation and renaturing of tRNA transcripts and ASLs did not alter their abilities to bind the 30S subunits. Small ribosomal subunits (30S) were prepared and activated according to Ericson et al. (*J. Mol. Biol.* 250: 407–419 (1995)).

Binding of tRNAs and ASLs to 30S ribosomal subunits. In order to determine the $K_d$ of tRNA and ASL binding to the ribosome, 30S subunits (10 pmol) and poly(U), poly(A), poly(AG) or poly(AC) (10 μg) were incubated for 20 minutes at 37° C. with increasing amounts of $^{32}$P-labeled tRNA or ASL (up to 50 pmol) in 40 ml of CMN buffer (80 mM potassium-cacodylate, pH 7.2, 20 MM MgCl$_2$, 100 mM NH$_4$Cl, and 3 mM β-mercaptoethanol). The reaction was incubated for another 20 minutes on ice, passed through nitrocellulose filters (0.45 μm) and the filter-bound RNA washed twice with ice-cold buffer (100 μl). The filters were then air-dried and counted. $K_d$s and their standard deviations were determined using non-linear regression analysis on four replicates of each experiment.

Chemical modification and primer extension. Chemical probing and primer extension was accomplished as described by Moazed and Noller (*J. Mol. Biol.* 211: 135–145 (1990)) except that the modifications with both dimethyl sulfate and kethoxal were conducted at 20° C. for 30 minutes in 40 ml of CMN buffer. Ribosomal 30S subunits (10 pmol) programmed with poly(U), poly(A), or poly(AG) (10 mg) were incubated with 50 pmoles yeast tRNA$^{Phe}_{GmAA}$ or ASL$^{Phe}_{GAA}$ or 150 pmoles of E. coli tRNA$^{Lys}_{SUU}$, human ASL$^{Lys3}_{SUU}$, or human ASL$^{Lys3}_{UUU}$.

UV and NMR Spectroscopy. Thermal denaturations of tRNA$^{Lys}$ ASLs were monitored with UV and NMR spectroscopies. The UV samples contained ~2 M (0.3 A$_{260}$ units) RNA in 10 mM sodium phosphate buffer, pH 7.2, 100 mM NaCl and 0.1 mM EDTA. NMR samples contained ~0.1 mM (11.5 A$_{260}$ units) RNA in 10 mM phosphate buffer, pH 6.0, and 0.1 mM EDTA. Double quantum filtered COSY (DQF-COSY) experiments were conducted at 10° C. with a Bruker DRX 500 MHz spectrometer using standard procedures (Rance et al., *Biochem. Biophys. Res. Commun* 117: 479–485 (1983)). The exchangeable and non-exchangeable proton resonances were assigned using standard procedures except for the imino protons of $U_{34}$, $U_{35}$ and $U_{36}$ which were assigned via site-specific incorporation of $^{15}$N3-uridines. Resonances of $ASL_{LysSUU}$ were assigned by comparison to the spectra of $ASL^{Lys}_{SUU}$.

2. Results

Figure 2A:
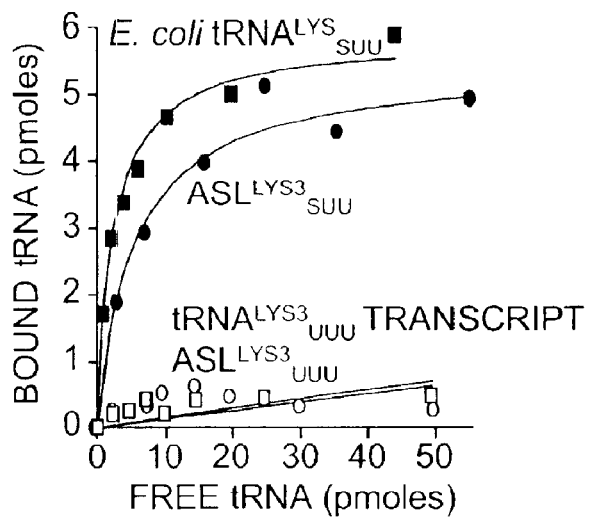
FIG. 2. Binding of tRNAs and anticodon/stem loops (ASLs) to programmed 30S ribosomal subunits. Ribosome binding assays were carried out as described under Materials and Methods by using $^{32}$P-labeled tRNAs or ASLs and appropriately programmed 30S ribosomal subunits. A: Binding of lysine tRNAs and ASLs to poly(A)-programmed 30S ribosomal subunits: (filled square) native E. coli $tRNA^{Lys}_{SUU}$; (open square) human $tRNA^{Lys3}_{UUU}$ transcript; (filled circle) $ASL^{Lys3}_{SUU}$; and (open circle) $ASL^{Lys3}_{UUU}$. B: Binding of (filled squre) E. coli $tRNA^{Glu}_{SUC}$, and (open diamond) E. coli $tRNA^{Glu}_{UUC}$ transcript to poly(AG)-programmed 30S ribosomal subunits, and (open triangle) E. coli tRNA-$Gln_{UUG}$ transcript to poly(AC)-programmed 30S ribosomal subunits. C: Binding of (filled square), native yeast tRNA$^{Phe}_{GmAA}$ and (opened square), ASL$^{Phe}_{GAA}$ to poly(U)-programmed 30S ribosomal subunits. $G_m = 2'O$-methylguanosine.
Figure 2B:
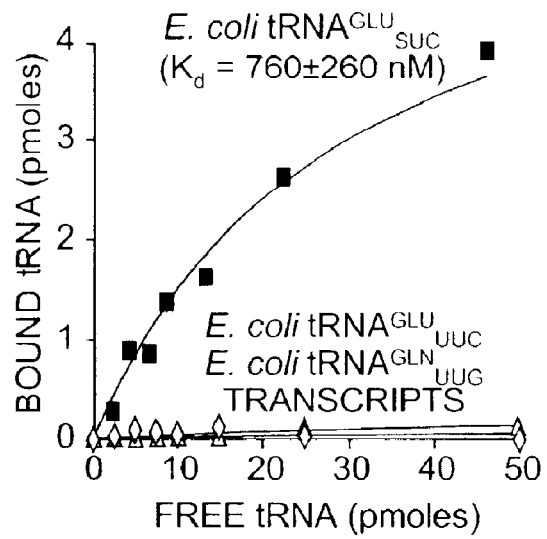
Figure 2C:
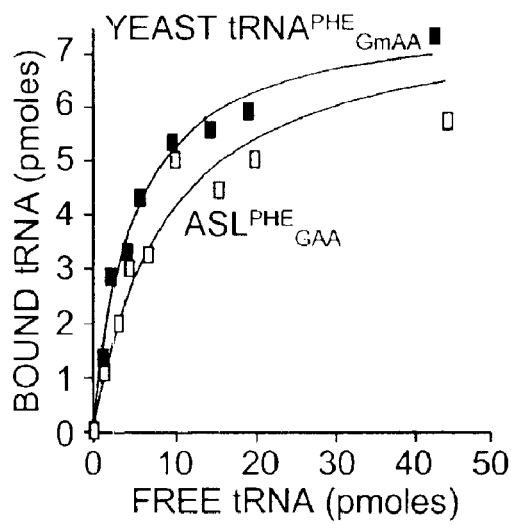

Ribosomal Binding of Native tRNAs, Unmodified tRNAs, and ASLs. The unmodified anticodon stem and loop of E. coli tRNA$^{Lys}_{UUU}$ ($ASL^{Lys}_{UUU}$) and that of tRNA-$^{Gln}_{UUG}$ ($ASL^{Gln}_{UUG}$) did not bind the appropriately programmed ribosomes, presumably because of lack of modified nucleosides (von Ahsen et al., RNA 3: 49–56 (1997)). However, rather than requiring one or more modified nucleosides, perhaps these particular ASLs failed to bind because their smaller sequences lacked a required structural element. Therefore, we compared the ribosome binding of the unmodified transcripts of the tRNAs to that of fully modified, native tRNAs. In vitro transcribed, full-length E. coli tRNA$^{Gln}_{UUG}$ and tRNA$^{Glu}_{UUC}$ and human tRNA$^{Lys3}_{UUU}$ all failed to bind the appropriately programmed 30S ribosomal subunits (FIGS. 2A and B). Under the same conditions, native E. coli tRNA$^{Lys}_{SUU}$ effectively bound poly(A)-programmed ribosomes (FIG. 2A), E. coli tRNA$^{Glu}_{SUC}$ bound randomly polymerized poly(AG)-programmed ribosomes (FIG. 2B), and yeast tRNA$^{Phe}_{GmAA}$ bound poly(U)-programmed ribosomes (FIG. 2C). Thus, the lack of ribosomol binding by unmodified E. coli lysine and glutamine ASLs (von Ahsen et al., supra) was not due to the size of the RNA used in these experiments. A similar negative result was observed for the transcript of tRNA$^{Lys}_{UUU}$ when ribosomes were programmed with randomized poly(AG) containing both the AAG and AAA codons (data not shown). Thus, the inability of unmodified ASLs and tRNA transcripts of lysine, glutamine, and glutamic acid to bind the ribosome was neither due to the sequence length nor a codon preference. Because of these results and the fact that fully modified tRNA$^{Lys}_{SUU}$, tRNA-$^{Gln}_{SUG}$ and tRNA$^{Glu}_{SUC}$ have in common s$^2$U derivatives at the wobble position 34, we postulated that s$^2$U$_{34}$-containing-tRNAs are dependent on nucleoside modifications for ribosome binding.

In order to test this hypothesis, heptadecamer ASLs corresponding to the human tRNA$^{Lys3}_{SUU}$ sequence were produced with and without s$^2$U$_{34}$ by automated oligonucleotide synthesis and then assayed for ribosome binding. Human and E. coli tRNA$^{Lys}_{SUU}$ ASLs have identical sequences except for the three base pairs at the top of the stem (Agris et al., RNA 3: 420–428 (1997)). Surprisingly, we found that the $ASL^{Lys3}_{SUU}$ (FIG. 1A), singularly modified with just s$^2$U at position 34, was able to bind poly(A)- and poly(AG)-programmed ribosomes almost as effectively as native E. coli tRNA$^{Lys}_{SUU}$ (FIG. 2A). In fact, the $K_d$ for the interaction of $ASL^{Lys3}_{SUU}$ with poly(A)-programmed 30S ribosomal subunits (176±62 nM) was comparable to that of native E. coli tRNA$^{Lys}_{SUU}$ (70±7 nM). As expected, the unmodified human $ASL^{Lys3}_{UUU}$ (FIG. 1A) did not bind AAA- or AAG-programmed ribosomes (FIG. 2A). In contrast, unmodified yeast $ASL^{Phe}_{GAA}$ bound poly(U)-programmed 30S ribosomal subunits as effectively ($K_d$=136±49 nM) as native tRNA$^{Phe}_{GmAA}$ ($K_d$=103±19 nM) (FIG. 2C).

Figure 3A:
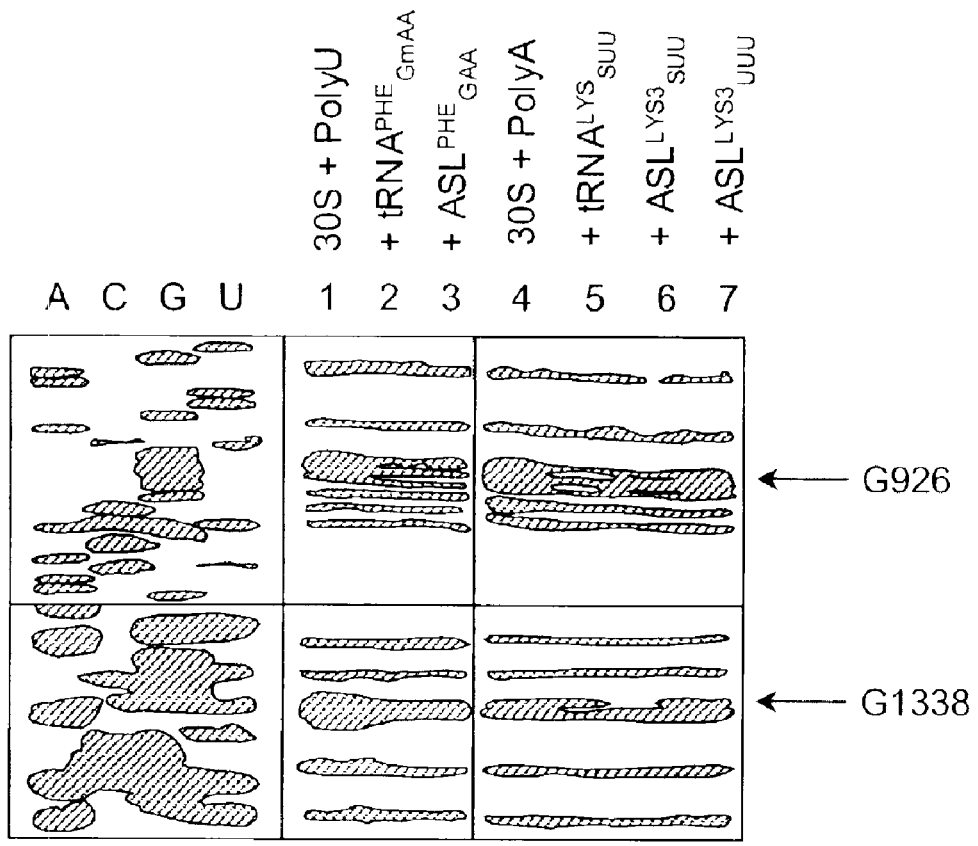
FIG. 3. Footprinting of tRNAs and ASLs at the 16S rRNA P-site. A: Chemical probing experiments were conducted with kethoxal, as described under Materials and Methods, with: poly(U)- (lanes 1–3) or poly(A)-programmed (lanes 4–7) 30S ribosomal subunits plus native yeast tRNA$^{Phe}_{GmAA}$ (lane 2); ASL$^{Phe}_{GAA}$ (lane 3); E. coli tRNA$^{Lys3SUU}$ (lane 5); ASL$^{Lys3}_{SUU}$ (lane 6); or ASL$^{Lys3}_{UUU}$ (lane 7). B: Dimethyl sulfate protection experiments were conducted with poly (A)-programmed (lanes 1–4) 30S ribosomal subunits plus E. coli tRNA$^{Lys}_{SUU}$ (lane 2); ASL$^{Lys3}_{SUU}$ (lane 3); or ASL$^{Lys3}_{UUU}$ (lane 4), as described under Materials and Methods.
Figure 3B:
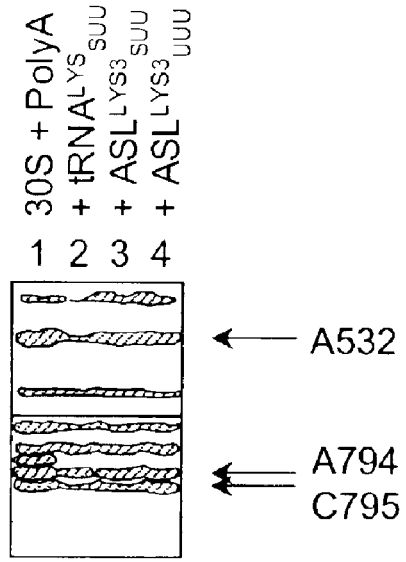

16S P-site footprints by tRNAs and ASLs. To determine if the $ASL^{Lys3}_{SUU}$ bound the ribosome at the same site as fully modified tRNA$^{Lys}_{SUU}$, we conducted a chemical footprinting analysis of the ASL and tRNA on 16S rRNA. Chemical protections were analyzed for five of the commonly recognized 16S P-site nucleotides (A532, G926, A794, C795, and G1338) (Moazed and Noller, supra). The $ASL^{Lys3}_{SUU}$ produced the same footprint on 16S rRNA as did the native E. coli tRNA$^{Lys}_{SUU}$ (FIGS. 3A and B). Both ASL and tRNA protected all five P-site nucleosides. Of the five 16S rRNA nucleosides that were probed, A532, G926 and G1338 were intrinsically more reactive to chemical probes than A794 and C795. Hence, they were more easily recognized as being protected in the presence of ASL or tRNA (FIG. 3B). The reduced chemical reactivities and the weaker protections of A794 and C795 have also been documented by others (Moazed and Noller, supra). As expected, the unmodified $ASL^{Lys3}_{UUU}$ provided no substantial protection of P-site nucleotides from either kethoxal (FIG. 3A) or dimethyl sulfate (FIG. 3B) chemical probes. In contrast, the unmodified yeast $ASL^{Phe}_{GAA}$ produced the same footprint as did native yeast tRNA$^{Phe}_{GmAA}$, the $ASL^{Lys3}_{SUU}$ and native E. coli tRNA$^{Lys}_{SUU}$. Thus, as shown by both filter binding and chemical probing, for some tRNAs, such as tRNA$^{Lys}_{SUU}$, but not all, the nucleoside modifications are critical for ribosomal P-site binding.

Figure 4A:
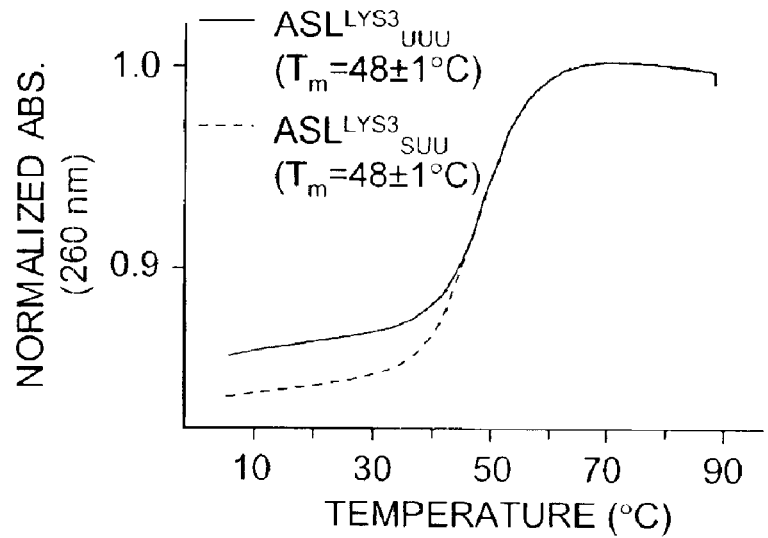
FIG. 4. Thermal denaturation analyses of ASL$^{Lys3}_{SUU}$ and ASL$^{Lys3}_{UUU}$. A: UV thermal denaturation profiles of the ASLs (~2 µM) were obtained as described under Materials and Methods in 10 mM phosphate buffer, pH 7.2, containing 100 mM NaCl and 0.1 mM EDTA. B: Imino proton NMR spectra of ASL$^{Lys3}_{SUU}$ and ASL$^{Lys3}_{UUU}$ as a function of temperature. The spectra were collected on ~0.1 mM ASLs in 10 mM phosphate buffer, pH 6.0 containing 0.1 mM EDTA.
Figure 4B:
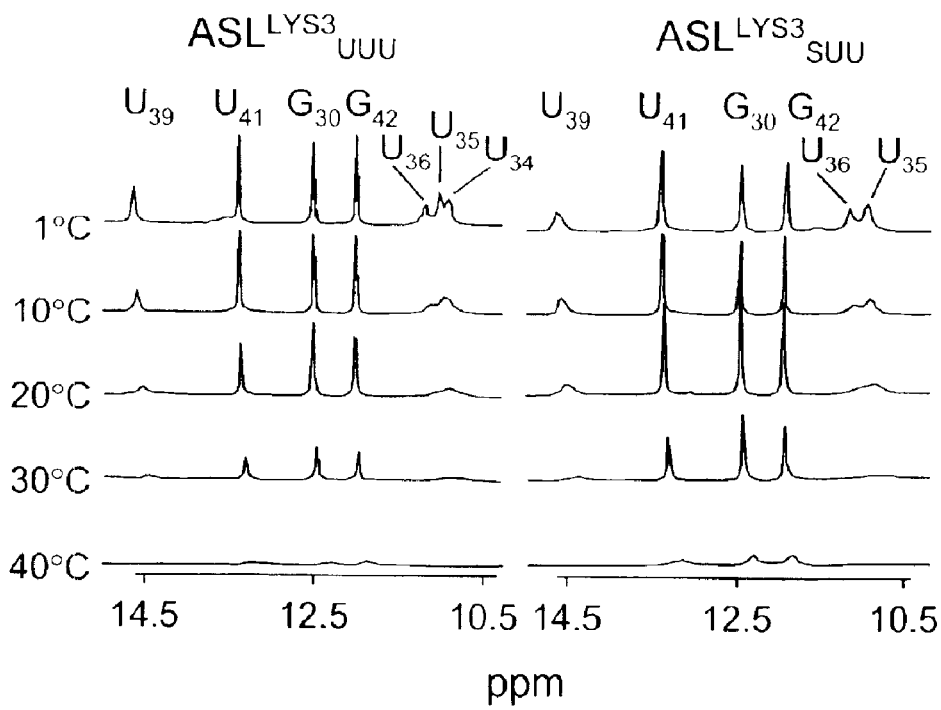
Figure 5A:
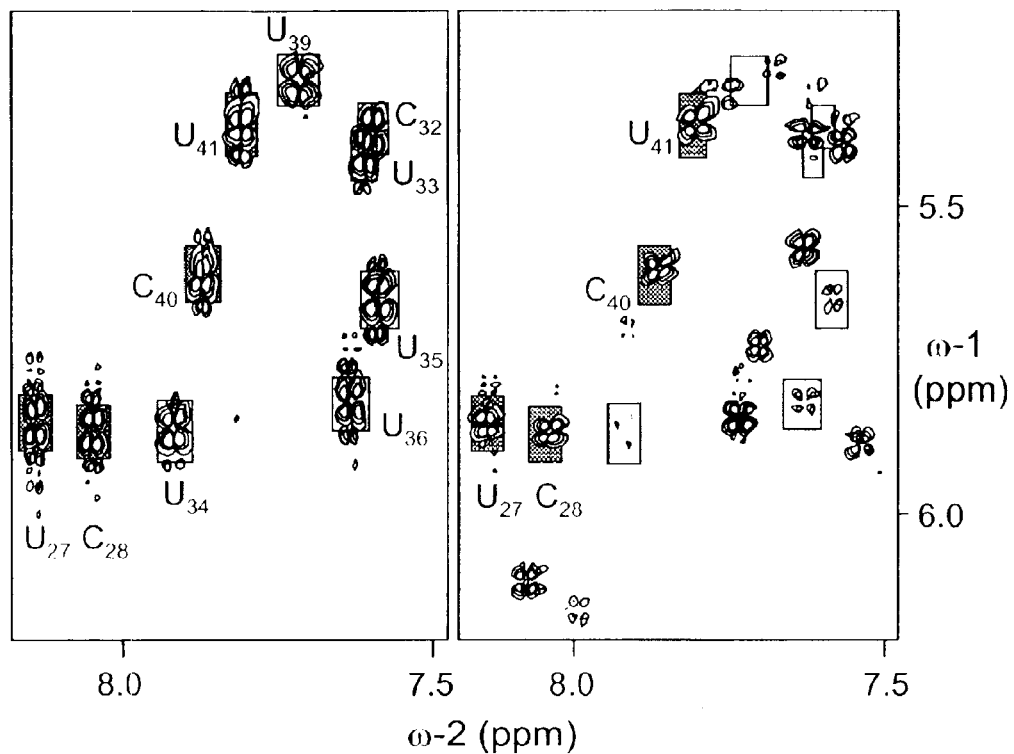
FIG. 5. A: Comparison of the 500-MHz DQF-COSY spectra of ASL$^{Lys3UUU}$ and ASL$^{Lys3}_{SUU}$ in the region showing cross peaks between H5–H6 protons. Boxes, placed behind the cross-peaks in the ASL$^{Lys3UUU}$ spectrum and in the corresponding positions in ASL$^{Lys3}_{SUU}$ spectrum facilitate comparison. B: Shaded boxes indicate stem pyrimidine H5–H6 cross-peaks that were not affected by the s$^2$U-modification. Cross-peaks observed outside the boxes in the ASL$^{Lys3}_{SUU}$ spectrum were from the loop pyrimidines of ASL$^{Lys3}_{SUU}$ and due to a dynamic equilibrium of the loop this ASL. A small impurity of ASL$^{Lys3}_{UUU}$ (<10%) in the ASL$^{Lys3}_{SUU}$ sample was responsible for weak cross-peaks inside open boxes in the ASL$^{Lys3SUU}$ spectrum.
Figure 5B:
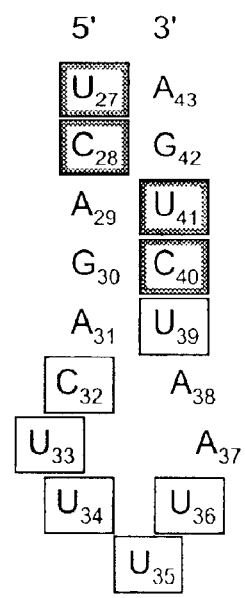

UV and NMR Spectroscopies. The dramatic restoration of ribosomal binding activity by a single, simple base modification underscores the importance of the 2-thio group in tRNA$^{Lys}_{SUU}$ and prompted us to examine possible structural differences between the unmodified $ASL^{Lys3}_{UUU}$ and the $ASL^{Lys3}_{SUU}$. Thermal denaturations, monitored by both UV spectroscopy and the imino proton chemical shifts of NMR spectra (FIGS. 4A and B), failed to detect any significant differences in the stability of the ASLs. The ASLs had similar denaturation profiles and identical melting points ($T_m$=48±1° C.). These results were not surprising considering that the techniques employed principally monitored the stabilities of ASL stems and not the loops. However, structural and dynamic differences between the two ASL loops became apparent in analysis of NMR spectra of non-exchangeable protons (FIG. 5). Examination of the DQF-COSY spectra of $ASL^{Lys3}_{UUU}$ and $ASL^{Lys3}_{SUU}$ revealed that H5–H6 cross-peaks arising from pyrimidines in the first four base pairs of the stem ($U_{27}$, $C_{28}$, $C_{40}$ and $U_{41}$) were not affected by the presence of s$^2$U$_{34}$ in the loop (FIGS. 5A and B). However, the remaining six pyrimidines of the modified $ASL^{Lys3}_{SUU}$, including five in the loop ($C_{32}$, $U_{33}$, $S^2U_{34}$, $U_{35}$ and $U_{36}$), produced more than six signals. These results suggest that the loop region of $ASL^{Lys3}_{SUU}$, unlike that of the unmodified $ASL^{Lys3}_{UUU}$, was engaged in a slow conformational equilibrium involving two or more species. We have yet to fully describe that equilibrium. However, there is no doubt that the presence of s$^2$U has changed the loop.

The results presented here are the first demonstration of a single atom modification (O→S) in tRNA that is critical for ribosomal binding. Thiolated human $ASL^{Lys3}_{SUU}$ binds the ribosome, yet unmodified E. coli $ASL^{Lys}_{UUU}$, the unmodified human tRNA$^{Lys3}_{UUU}$ transcript and the corresponding ASL do not. In addition, the unmodified transcripts of tRNA$^{Glu}_{UUC}$ and tRNA$^{Gln}_{UUG}$, as well as the unmodified $ASL^{Glu}_{UUG}$ (von Ahsen, supra), do not bind the ribosome. These results demonstrate the importance of the s$^2$U$_{34}$ nucleoside modification in the in vitro P-site binding of many S$^2$U$_{34}$-containing tRNAs, regardless of genus. In addition, asuE (trm U) mutants of E. coli [personal communication, Dieter Söll] and sin 3/sin 4 mutants of Schizosaccharomyces pombe (Grossenbacher et al., J. biol. Chem. 261: 16351–16355 (1986); Heyer et al., J. Biol. Chem. 259: 2856–2862 (1984)) deficient in the synthesis of s$^2$U grow very poorly, suggesting ribosomal binding of s$^2$U-containing tRNAs is modification dependent in vivo, as well as in vitro.

Figure 6:
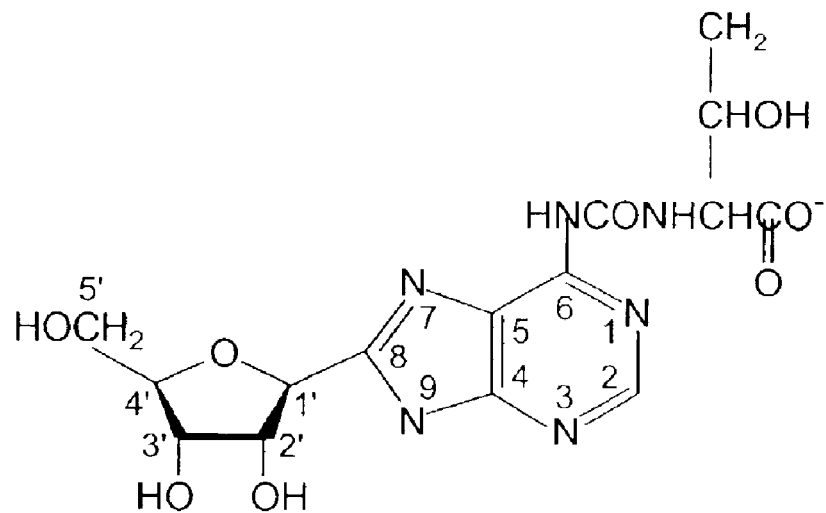
FIG. 6 is essentially the same as FIG. 2 above, but compared human ASL$^{Lys}_{UUU}$ with T$^6$A$_{37}$ with the unmodified ASL$^{Lys}_{UUU}$ with A$_{37}$. Again, significantly different ribosomal binding was found.
Figure 6:
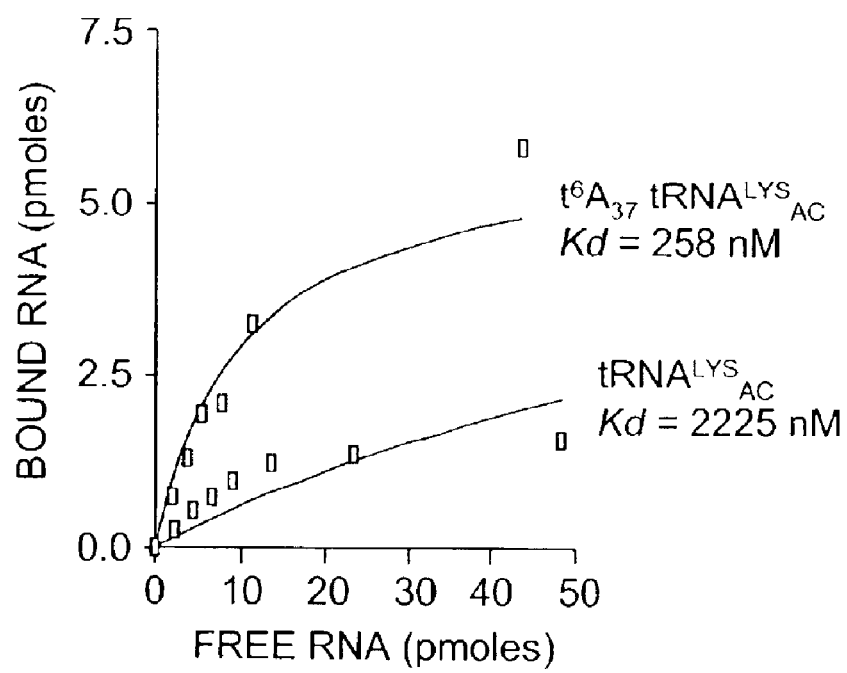

To provide further evidence for nucleoside modifications being targets for antibacterial drugs, ribosome binding of $ASL^{Lys}_{UUU}$ with $t^6A_{37}$ was compared to the unmodified $ASL^{Lys}_{UUU}$ with $A_{37}$. ($t^6A$ is N6-threonylcarbamoyladenosine). Studies were carried out in essentially the same manner as described in connection with FIG. 2 above and these data are presented in FIG. 6. Again, the modified nucleotide, this time at position 37, was critical for ribosome binding. These data indicate that modified nucleoside throughout the stem-loop structure may be targeted for drug binding, interaction and screening as described above.

The foregoing is illustrative of the present invention, and is not to be construed as limiting thereof The invention is defined by the following claims, with equivalents of the claims to be included therein.

That which is claimed is:

1. A method of screening for compounds useful for inhibiting retrovirus propagation in a host for said retrovirus, wherein said retrovirus primes reverse transcription in said host by binding of a specific host tRNA to retrovirus RNA at a pair of separate binding sites on said host tRNA, said method comprising:

contacting in vitro said specific host tRNA to said retrovirus RNA in the presence of said test compound; and then;

determining whether said test compound inhibits the binding of said specific host tRNA to said retrovirus RNA;

the inhibition of binding indicating said test compound is useful for inhibiting propagation of said virus in said host;

whereby mutation of said retrovirus RNA to bind an alternate host tRNA for priming of reverse transcription requires a pair of mutations at a pair of separate tRNA binding sites in said retrovirus RNA.

2. A method according to claim 1, wherein said determining step comprises determining whether said compound inhibits the binding of said tRNA to said retrovirus RNA at position 27–43 of said tRNA.

3. A method according to claim 1, wherein said specific host tRNA is $tRNA^{lys}_{suu}$.

4. A method according to claim 3, wherein said determining step comprises determining whether said compound inhibits the binding of $tRNA^{lys}_{suu}$ at position 34 thereof to said retrovirus RNA.

5. A method of screening for compounds useful for inhibiting retrovirus propagation in a host for said retrovirus, wherein said retrovirus primes reverse transcription in said host by binding of a specific host tRNA to retrovirus RNA at a pair of separate binding sites on said host tRNA, wherein said specific host tRNA is $tRNA^{lys}_{suu}$;

said method comprising:

contacting in vitro said specific host tRNA to said retrovirus RNA in the presence of said test compound; and then;

determining whether said compound inhibits the binding of said specific host tRNA to said retrovirus RNA at position 27–43 of said tRNA in the presence of said test compound;

the inhibition of binding indicating said test compound is useful for inhibiting propagation of said virus in said host;

whereby mutation of said retrovirus RNA to bind an alternate host tRNA for priming of reverse transcription requires a pair of mutations at a pair of separate tRNA binding sites in said retrovirus RNA.

* * * * *

UNITED STATES PATENT AND TRADEMARK OFFICE
CERTIFICATE OF CORRECTION

Page 1 of 1

PATENT NO. : 6,962,785 B2
APPLICATION NO. : 10/212905
DATED : November 8, 2005
INVENTOR(S) : Agris et al.

It is certified that error appears in the above-identified patent and that said Letters Patent is hereby corrected as shown below:

In the Specification:
Column 1, Lines 13-17: Please replace the entire paragraph to read as follows:

This invention was made with government support under grant number GM23037 awarded by the National Institutes of Health and grant number 9631103 awarded by the National Science Foundation. The government has certain rights to this invention.

Signed and Sealed this
First Day of July, 2014

Michelle K. Lee
*Deputy Director of the United States Patent and Trademark Office*